US006924397B2

(12) United States Patent
Nugent et al.

(10) Patent No.: US 6,924,397 B2
(45) Date of Patent: Aug. 2, 2005

(54) PROCESS FOR THE PREPARATION OF α-CHLOROKETONES FROM ALKYL ESTERS

(75) Inventors: William Aloysius Nugent, Wilmington, DE (US); Dengjin Wang, Levittown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/690,771

(22) Filed: Oct. 22, 2003

(65) Prior Publication Data

US 2005/0090670 A1 Apr. 28, 2005

(51) Int. Cl.$^7$ ............... C07C 45/00; C07C 325/00; C07C 233/00
(52) U.S. Cl. ............ 568/314; 568/316; 568/346; 568/348; 568/397; 568/20; 564/123; 564/161; 564/209
(58) Field of Search ............... 568/314, 316, 568/346, 348, 397, 20; 564/123, 161, 209

(56) References Cited

U.S. PATENT DOCUMENTS

| | | | |
|---|---|---|---|
| 5,849,911 A | 12/1998 | Fässler et al. | 544/335 |
| 6,399,793 B1 | 6/2002 | Kronenthal et al. | 549/519 |

OTHER PUBLICATIONS

Corey, E.J. et al., "Formation and Photochemical Rearrangement of β-Ketosulfoxonium Ylides", J. Am. Chem. Soc., vol. 86, pp. 1640–1641 (1964).

Carey, F.A. et al., Advanced Organic Chemistry, Fourth Edition, Part A: Structure and Mechanisms, Kluwer Academic/Plenum Publishers, publ., p. 473 (2000).

Chen, P. et al., "A Practical Method for the Preparation of α'–Chloroketones of N–Carbamate Protected–α–Aminoacids", Tetrahedron Letters, vol. 38, No. 18, pp. 3175–3178 (1997).

Corey, E.J. et al., "A New Synthetic Approach to Medium–Sized Carbocyclic Systems", J. Am. Chem. Soc., vol. 86, pp. 1641–1642 (1964).

DeGraw, J.I. et al., "α–Acetoxy and α–Halomethylketones from Acyloxosulfonium Ylides", Tetrahedron Letters, No. 20, pp. 2501–2502 (1968).

Greene, T.W. et al., Protective Groups in Organic Synthesis, Third Edition, John Wiley & Sons, Inc., publ. (1999) (table of contents).

König, H. et al., "Über neue, stabile Schwefel–Ylide", Chem. Ber., vol. 98, pp. 3733–3747 (1965).

Kowalski, C.J. et al., "Bromomethyl Ketones and Enolates: Alternative Products From Ester Homologation Reactions", J. Org. Chem., vol. 50, pp. 5140–5142 (1985).

Kowalski, C.J. et al., "Ester Homologation Revisited: A Reliable, Higher Yielding and Better Understood Procedure", J. Org. Chem., vol. 57, pp. 7194–7208 (1992).

Nagao, Y. et al., "A New Design for Chiral Induction: A Highly Regioselective Differentiation between Two Identical Groups in an Acyclic Compound Having a Prochiral Center", J. Am. Chem. Soc., vol. 104, pp. 2079–2081 (1982).

Powers, J.C. et al., "Design and Synthesis of Inhibitors for Crystallographic Studies on the Active Site of Chymotrypsin", Journal of the American Chemical Society, vol. 92, No. 6, pp. 1782–1783 (1970).

Primary Examiner—Johann Richter
Assistant Examiner—Sikarl A. Witherspoon
(74) Attorney, Agent, or Firm—Henry H. Gu; Deanna L. Baxam

(57) ABSTRACT

The present invention relates to a process for the preparation of α-chloroketones from readily available alkyl esters by the reaction of a sulfoxonium ylide on said alkyl esters to generate a keto sulfoxonium ylide that is in turn treated with anhydrous HCl.

47 Claims, No Drawings

PROCESS FOR THE PREPARATION OF α-CHLOROKETONES FROM ALKYL ESTERS

FIELD OF THE INVENTION

The present invention relates to a novel process for the preparation of α-chloroketones from alkyl esters. The α-chloroketones produced in accordance with the process of the invention are useful precursors of many pharmaceutical compounds.

BACKGROUND OF THE INVENTION

Two procedures are commonly used for the conversion of carboxylic acid derivatives to α-chloroketones, an important family of pharmaceutical intermediates. In the first approach, exemplified by Powers and Wilcox, *J. Am. Chem. Soc.*, Vol. 92, page 1782, 1970, the carboxylic acid is converted to an acid chloride, which is then treated with diazomethane and finally with hydrogen chloride. However, diazomethane is a highly toxic and explosive gas, making this approach problematic for large-scale manufacture of α-chloroketones. Kowalski et. al., *J. Org. Chem.*, Vol. 50, 5140, 1985 and Vol. 57, 7194, 1992 describe homologation of esters to α-haloketones utilizing the system $CH_2Br_2$/LDA/n-BuLi. Chen and Cheng, *Tetrahedron Letters*, Vol. 38, No. 18, pages 3157–3178, 1997 subsequently disclosed that higher yields could be achieved by substituting iodochloromethane for dibromomethane in the preceding process. However, this approach is disadvantageous in that cryogenic temperatures are required and, in the latter case, toxic and high-boiling chlorodiiodomethane is a side-product. Thus it is evident that a need exists for a safe and efficient process for the manufacture of α-chloroketones.

A process for preparing α-haloketones is described by König and Mezger in *Chem. Ber.*, Vol. 98, pages 3733–3747, 1965. The disclosed process involves the reaction of dimethylsulfoxonium methylide with isocyanates and ketenes to form β-keto sulfoxonium ylides. On page 3738, in Table 3, there is disclosed treatment of the β-keto sulfoxonium methylides with hydrochloric acid or bromine to form α-chloroketone or α,α-dibromoketone. Subsequently, Degraw and Cory, *Tetrahedron Letters*, No. 20, pages 2501–2502, 1968, disclosed the preparation of α-acetoxy and α-halomethylketones by the action of acids on acyloxosulfonium ylides generated by other means.

Corey and Chaykovsky, *J. Am. Chem. Soc.*, Vol. 86, pages 1640–1641, 1964 found that the ethyl ester of an α,β-unsaturated acid but which did not contain a fluorine substituent did not react with dimethylsulfoxonium methylide at the ester functionality. Instead the sulfur ylide underwent Michael addition to the C═C double bond. In contrast, these authors teach that phenyl esters of typical (non-fluorine-containing) carboxylic acids do react with dimethylsulfoxonium methylide to form β-keto sulfoxonium ylides. In similar fashion Nagao et. al., *J. Am. Chem. Soc.*, Vol. 104, No. 7, pages 2079–2081, 1982 examined the reaction of the methyl ester of a non-fluorine-containing carboxylic acid with dimethylsulfoxonium methylide. Again no reaction of the ester functionality is observed and the reagent instead effects cleavage of a carbon-nitrogen bond elsewhere in the molecule. The different behavior of the fluorine-containing esters is consistent with the fact that fluorine is by far the most electronegative element on the periodic table. Based on these precedents, one skilled in the art might reasonably conclude that fluorine substitution is required to promote the homologation of alkyl esters to β-keto sulfoxonium ylides by treatment with dimethylsulfoxonium methylide.

Consistent with this supposition, Kronenthal and Schwinden, U.S. Pat. No. 6,399,793, discloses a process for the preparation of α'-N-acyl-α'-chloroketones using phenyl esters as starting material. This reference does not, however, teach or suggest preparation of the sulfoxonium ylides using readily available alkyl esters such as methyl or ethyl esters, though such starting materials would present desirable advantages. These advantages include the fact that alkyl esters can be prepared directly from the corresponding acids without the intermediacy of a hydrolytically sensitive acid chloride as well as the formation of volatile alcohols as side products upon treatment with dimethylsulfoxonium methylide, which simplifies product isolation. Such a desirable preparation has now been achieved in the present invention.

SUMMARY OF THE INVENTION

The present invention is directed to an improved process for the preparation of α-chloroketones from readily available alkyl esters by the reaction of a sulfoxonium ylide on said alkyl esters to generate a keto sulfoxonium ylide that is in turn treated with anhydrous HCl.

DETAILED DESCRIPTION OF THE INVENTION

The process of the present invention provides an advantageous synthesis of the α-chloroketones represented by formula I:

wherein R is alkyl or substituted alkyl, cycloalkyl or substituted cycloalkyl, aryl or substituted aryl, or heterocycle or substituted heterocycle, provided that said heterocycle is attached to —(C═O)$CH_2$Cl group at any available ring carbon atom.

The compounds represented by formula I are useful as intermediates in the synthesis of molecules that are inhibitors of ACE, renin and HIV proteases. Such compounds and their uses are disclosed, for example, in U.S. Pat. No. 5,849,911, the entire disclosure of which is incorporated herein by reference.

The following are definitions of terms used in the present specification. The initial definition provided for a group or term herein applies to that group or term throughout the present specification individually or as part of another group, unless otherwise indicated.

The terms "alkyl" or "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "$C_1$–$C_4$ alkyl," for example, refers to a straight or branched chain alkane (hydrocarbon) radical containing from 1 to 4 carbon atoms, such as methyl, ethyl, propyl, isopropyl, n-butyl, t-butyl, isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen, trifluoromethyl, trifluoromethoxy, cyano, nitro, alkyl, cycloalkyl, heterocycle, aryl, $OR_a$, $SR_a$, $S(=O)R_e$, $S(=O)_2R_e$, $S(=O)_2R_e$, $P(=O)_2R_e$, $NR_bR_c$, $NR_bS(=O)_2R_e$, $NR_bP(=O)_2R_e$, $S(=O)_2NR_bR_c$, $P(=O)_2NR_bR_c$, $C(=O)R_a$, $C(=O)NR_bR_c$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle; and $R_e$ is alkyl, cycloalkyl, alkenyl, cycloalkenyl, alkynyl, heterocycle, or aryl. In the aforementioned exemplary substitutents, groups such as alkyl, cycloalkyl, alkenyl, alkynyl, cycloalkenyl, heterocycle and aryl can themselves be optionally substituted. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, the aforementioned cycloalkyl, cycloalkenyl, heterocycle and aryl can themselves be optionally substituted.

The term "alkenyl" refers to a straight or branched chain hydrocarbon radical containing from 2 to 12 carbon atoms and at least one carbon-carbon double bond. Exemplary such groups includes ethenyl or allyl. "Substituted alkenyl" refers to an alkenyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "alkynyl" refers to a straight or branched chain hydrocarbon radical containing from 2 to 12 carbon atoms and at least one carbon to carbon triple bond. Exemplary such groups include ethynyl. "Substituted alkynyl" refers to an alkynyl group substituted with one or more substituents, preferably 1 to 4 substituents, at any available point of attachment. Exemplary substituents include, but are not limited to, alkyl or substituted alkyl, as well as those groups recited above as exemplary alkyl substituents.

The term "cycloalkyl" refers to a fully saturated cyclic hydrocarbon group containing from 1 to 4 rings and 3 to 8 carbons per ring. Exemplary such groups include cyclopropyl, cyclobutyl, cyclopentyl, cyclohexyl, cycloheptyl, etc. "Substituted cycloalkyl" refers to a cycloalkyl group substituted with one or more substituents, preferably 1 to 4 substituents, at any available point of attachment. Exemplary substituents include, but are not limited to, nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached heterocycle (excluding heteroaryl), fused cycloalkyl, fused heterocycle, or fused aryl, the aforementioned cycloalkyl, heterocycle and aryl can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to nitro, cyano, alkyl or substituted alkyl, as well as those groups recited above as exemplary alkyl substituents. Exemplary substituents also include spiro-attached or fused cylic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, the aforementioned cycloalkyl, cycloalkenyl, heterocycle and aryl can themselves be optionally substituted.

The term "aryl" refers to cyclic, aromatic hydrocarbon groups which have 1 to 5 aromatic rings, especially monocyclic or bicyclic groups such as phenyl, biphenyl or naphthyl. Where containing two or more aromatic rings (bicyclic, etc.), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, nitro, cycloalkyl or substituted cycloalkyl, cycloalkenyl or substituted cycloalkenyl, cyano, alkyl or substituted alkyl, as well as those groups recited above as exemplary alkyl substituents. Exemplary substituents also include fused cylic, especially fused cycloalkyl, fused cycloalkenyl, fused heterocycle, or fused aryl, the aforementioned cycloalkyl, cycloalkenyl, heterocycle and aryl can themselves be optionally substituted.

The terms "heterocycle" refers to fully saturated, or partially or fully unsaturated, including aromatic (i.e., "heteroaryl") cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, acridinyl, phenanthridinyl, xanthenyl and the like.

"Substituted heterocycle" refers to heterocycle groups substituted with one or more substituents, preferably 1 to 4 substituents, at any available point of attachment. Exemplary substituents include, but are not limited to, cycloatkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, the aforementioned cycloalkyl, cycloalkenyl, heterocycle and aryl can themselves be optionally substituted.

The terms "halogen" or "halo" refer to chlorine, bromine, fluorine or iodine.

The term "protecting group on the amino function" refers to an art-recognized group of moieties that can be attached to an amino group to keep it from being involved in reactions taking place elsewhere on the moiety to which it is attached. Art-recognized amino function protecting groups include, but not limited to, alkoxycarbonyl or aryloxycarbonyl groups, e.g., ethyloxycarbonyl; alkcarbonyl or arylcarbonyl, e.g., MeC(=O), or Ph(=O); and benzyl. Preferred among such groups is tert-butoxycarbonyl (BOC) and benzyloxycarbonyl (CBZ). Suitable protecting groups for the methods and compounds described herein include, without limitation, those described in standard textbooks, such as Greene, T. W. et al., Protective Groups in Organic Synthesis, Wiley, N.Y. (1999).

Unless otherwise indicated, any heteroatom with unsatisfied valences is assumed to have hydrogen atoms sufficient to satisfy the valences.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

Throughout the specifications, groups and substituents thereof may be chosen to provide stable moieties and compounds.

The process of the instant invention is readily carried out as described below. Solvents, temperatures, pressures, and other reaction conditions may readily be selected by one of ordinary skill in the art. Starting materials are commercially available or readily prepared by one of ordinary skill in the art.

The starting materials for the process of preparing α-chloroketones in accordance with the present invention are alkyl esters represented by the formula (II),

wherein R is as defined as above, $R_5$ is alkyl, preferably $C_1$–$C_6$ alkyl, more preferably $C_1$–$C_4$ alkyl.

In accordance with the process of the present invention, the starting material represented by formula (II) above is reacted with a sulfoxonium ylide, i.e. a compound containing a function represented by the formula (III)

to produce a keto sulfoxonium ylide represented by the formula (IV)

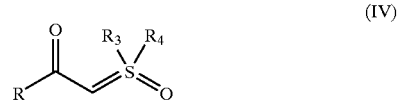

wherein R is as defined above and $R_3$ and $R_4$ are selected from the group consisting of alkyl, substituted alkyl, aryl and substituted aryl. The sulfoxonium ylide is conveniently prepared from a sulfoxonium salt by reaction with a suitable base in an organic solvent. Suitable sulfoxonium salts include trialkyl sulfoxonium halides, such as trimethylsulfoxonium iodide. Preferable bases include, for example, sodium hydride, potassium tert-butoxide and potassium tert-amylate, with the latter being particularly preferred. The reaction is carried out in an organic solvent such as dimethylformamide, tetrahydrofuran or, preferably, toluene with mild heating, i.e. at a temperature of from about 60° C. to about 80° C., preferably about 70° C. The preferred sulfoxonium ylide of formula (III) is where $R_3$ and $R_4$ are methyl.

Once the sulfoxonium ylide reagent is formed, it is reacted with the starting material represented by formula II above, optionally in the presence of a co-solvent. Useful co-solvents are aprotic solvents which are themselves inert toward the sulfur ylide. These include but are not limited to tetrahydrofuran, DMF, toluene, chlorobenzene, methyl t-butyl ether and dioxane. As an example of the use of a mixed solvent reaction medium, the reaction of the trialkylsulfoxonium compound and base is carried out in toluene as described, the resulting solution is cooled to about 0° C., and then added to a solution of the starting material in tetrahydrofuran to form the keto sulfoxonium ylide intermediate compound represented by formula (IV) above.

The keto sulfoxonium ylide compound represented by formula (IV) is then converted to the subject α-chloroketones of formula (1) by reaction with anhydrous HCl. The anhydrous HCl can be generated in situ by reacting a source of chloride, preferably a basic source of chloride, most preferably lithium chloride, with an organic acid, for example, methanesulfonic acid. The reaction is carried out in an organic solvent, such as tetrahydrofuran, toluene, or acetonitrile. The reaction is initiated at low temperature, i.e.

from about 0° C. to about 5° C. As the reaction proceeds, however, the temperature is raised to about 65° C. In addition, commercially available anhydrous HCl, such as 4 M HCl in dioxane, or gaseous anhydrous HCl can also be used.

EXAMPLE 1

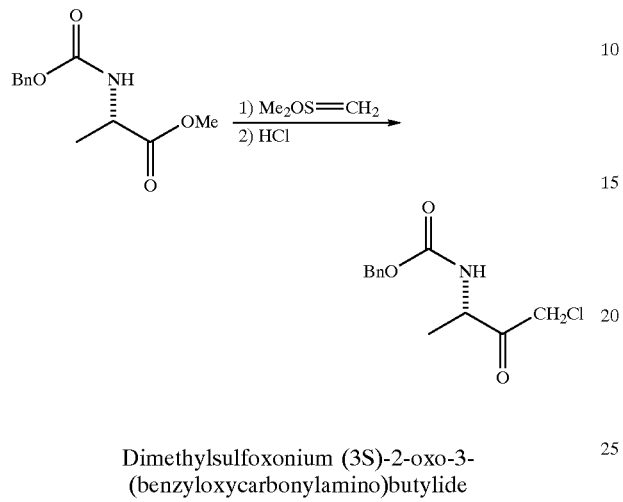

Dimethylsulfoxonium (3S)-2-oxo-3-(benzyloxycarbonylamino)butylide

A solution of 1.0 M potassium t-butoxide in THF (60 mL, 60 mmol) was added at room temperature to a suspension of trimethylsulfoxonium chloride (7.72 g; 60 mmol) in THF (40 mL). The mixture was heated at reflux for 2 hr and was then cooled to 0° C. A solution of CBZ-alanine methyl ester (4.74 g, 20 mmol) in THF (10 mL) was added dropwise at 0° C. and the resultant solution was stirred for 4 h at 0° C. The reaction was quenched with water (20 mL). The organic layer was separated and washed with brine (2×20 ml). The solvent was removed at reduced pressure to afford the crude sulfur ylide (5.76 g, 97%) as an off-white solid. $^1$H NMR: δ 1.30 (d, J=16.6, 3H), 3.34 (s, 3H), 3.36 (s, 3H), 4.16 (m, 1H), 4.61 (S, 1H), 5.08 (s, 2H), 5.81 (d, J=7.0, 1H), 7.28 (m, 5H). $^{13}$C NMR: δ 20.29, 42.02, 42.19, 53.23, 66.67, 68.71, 109.78, 128.22, 128.67, 136.88, 155.91, 188.67.

(3S)-1-Chloro-3-(benzyloxycarbonylamino)-2-butanone

Dimethylsulfoxonium (3S)-2-oxo-3-(benzyloxycarbonylamino)butylide (6.18 g, 22.0 mmol) was dissolved in THF (100 mL) and the solution was cooled to 0° C. Lithium chloride (1.6 g, 25 mmol) and methanesulfonic acid (1.6 mL, 24 mmol) were added and the temperature was gradually increased to 70° C. The mixture was stirred for 4 h at 70° C. and then was cooled to room temperature. The reaction was quenched by addition of water (100 mL) at room temperature. The phases were separated and 2:1 heptane/ethyl acetate (100 mL) was added to the organic layer. To remove DMSO, the organic layer was washed with saturated NaHCO$_3$ (20 mL), water (2×20 mL) and brine (20 mL) and was dried over Na$_2$SO$_4$. Removal of solvent afforded the crude product (5.0 g). Crystallization of this material from hot 5:1 heptane/ethyl acetate (50 mL) afforded the chloroketone (3.93 g, 70%) as a snow-white solid. The enantiomeric excess was determined to be 99% by supercritical fluid chromatography (Chiralpak AD-H, 150×4.6 mm, 5μ particle size, 15% methanol in CO$_2$ mobile phase, 40° C., 2 mL/min, 150 bar). Retention times for the enantiomers were assigned using an authentic racemate as 3.00 and 3.18 min. $^1$H NMR: δ 1.44 (d, J=7.1, 3H), 4.32 (s, 2H), 4.64 (m, 1H), 5.12 (s, 2H), 5.48 (br s, 1H), 7.36 (m, 5H). $^{13}$C NMR: δ 17.78, 46.23, 53.67, 67.39, 128.35, 128.53, 128.80, 136.20, 155.89, 201.78.

EXAMPLE 2

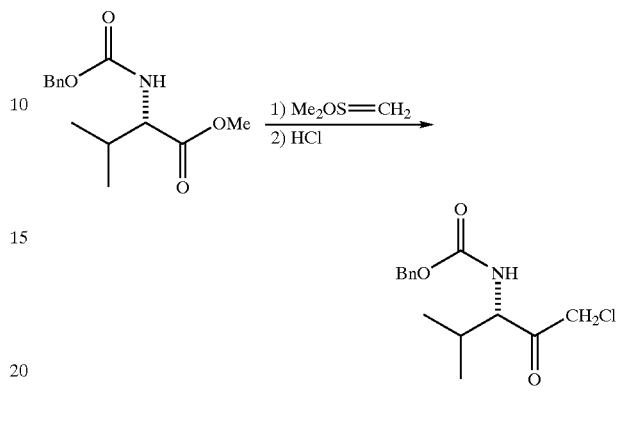

Dimethylsulfoxonium (3S)-2-oxo-3-(benzyloxycarbonylamino)-4-methylpentylide

A solution of 1.0 M potassium t-butoxide in THF (100 mL, 100 mL) was added at room temperature to a suspension of trimethylsulfoxonium chloride (12.68 g; 100 mmol) in THF (60 mL). The mixture was heated at reflux for 2 hr and was then cooled to $^{0°}$ C. A solution of CBZ-valine methyl ester (5.31 g, 20 mmol) in THF (10 mL) was added dropwise at 0° C. and the resultant solution was stirred for 4 h at 0° C. The reaction was quenched with water (20 mL). The organic layer was separated and washed with brine (2×20 ml). The solvent was removed at reduced pressure to afford the crude sulfur ylide (6.37 g, 98%) as an off-white solid. $^1$H NMR: δ 0.87 (d, J=7.1, 3H), 0.94 (d, J=7.1, 3H), 2.30 (m, 1H), 3.32 (s, 3H), 3.36 (s, 3H), 4.00 (m, 1H), 4.53 (s, 1H), 5.08 (s, 2H), 5.76 (d, J=3.65, 1H), 7.35 (m, 5H). $^{13}$C NMR: δ 17.86, 19.78, 32.07, 41.95, 42.20, 53.72, 62.59, 63.47, 66.76, 70.34, 128.22, 128.24, 128.67, 136.89, 156.60, 187.42, 187.64.

(S)-1-Chloro-3-(benzyoxycarbonylamino)-4-methyl-2-pentanone

Dimethylsulfoxonium (3S)-2-oxo-3-(benzyloxycarbonylamino)-4-methylpentylide. (6.51 g, 20.0 mmol) was dissolved in THF (100 mL) and the solution was cooled to 0° C. Lithium chloride (1.6 g, 25 mmol) and methanesulfonic acid (1.6 mL, 24 mmol) were added and the temperature was gradually increased to 70° C. The mixture was stirred for 48 hrs. at 70° C. and then cooled to room temperature. The reaction was quenched by addition of water (100 mL) at room temperature. The phases were separated and 2:1 heptane/ethyl acetate (100 mL) was added to the organic layer. To remove co-product DMSO, the organic layer was washed with saturated NaHCO$_3$ (20 mL), water (2×20 mL) and brine (20 mL) and was dried over Na$_2$SO$_4$. Removal of solvent afforded the crude chloroketone, which was purified by flash chromatography to yield the chloroketone (4.24 g, 75%) as an amber liquid. The enantiomeric excess was determined to be 90% by supercritical fluid chromatography (Chiralpak AD-H, 150× 4.6 mm, 5μ particle size, 15% methanol in CO$_2$ mobile phase, 40° C., 2 mL/min, 150 bar). Retention times for the enantiomers were assigned using an authentic racemate as 2.24 and 2.79 min. $^1$H NMR: δ 0.83 (d, 1=7.1, 3H), 1.02 (d, J=7.1, 3H), 2.19 (m, 1H), 4.21 (s, 2H), 4.55 (m, 1H), 5.10 (s, 1H), 5.41 (d, J=8.1, 1H), 7.35 (m, 5H). $^{13}$C NMR: δ 17.12, 19.93, 30.40, 47.50, 62.80, 67.52, 128.39, 128.56, 128.84, 136.26, 156.66, 201.61.

EXAMPLE 3

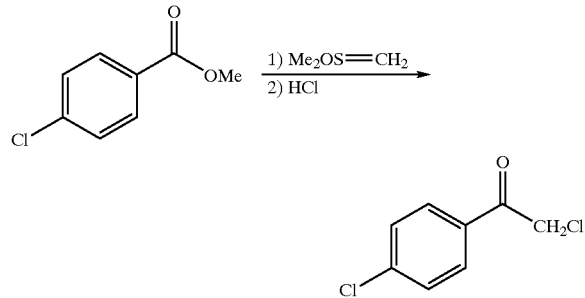

Dimethylsulfoxonium 2-oxo-(4-chlorophenyl)ethylide

To a 250 mL flask containing THF (100 mL) were added trimethylsulfoxonium iodide (6.6 g, 30 mmol) and 1.0 N potassium tert-butoxide in THF (30 mL, 30 mmol). The suspension was heated at reflux for 2 h then cooled to 0° C. whereupon methyl 4-chlorobenzoate (1.71 g, 10 mmol) was added in several portions over 10 min. The mixture was stirred for 2 h at 0° C. then overnight at room temperature. After removal of solvent at reduced pressure, water (10 mL) was added and the mixture was extracted with ethyl acetate (2×50 mL). The organic phase was washed with brine (2×10 mL), dried (Na$_2$SO$_4$), and the solvent was removed at reduced pressure to afford the crude product (2.3 g) as a white solid, which was used directly in the next step. $^1$H NMR: δ 3.52 (s, 6H), 4.94 (s, 1H), 7.33 (d, J=8.5, 2H), 7.71 (d, J=8.5, 2H). $^{13}$C NMR: 842.80, 68.91, 128.36, 128.76, 137.14, 137.68, 181.30.

2,4'-Dichloroacetophenone

A glass tube was charged with crude dimethylsulfoxonium 2-oxo-(4-chlorophenyl)ethylide (0.92 g, 4.0 mmol), THF (15 mL), and 4 M HCl in dioxane solution (1.15 mL, 4.6 mmol). The tube was sealed with a Teflon stopper and stirred at room temperature for 1 h then overnight in a 70° C. heated block at which time the mixture was homogeneous. The solvent was removed at reduced pressure and the residue was dissolved in hot methanol (4 mL). The solution was allowed to cool to room temperature and then to 5° C. to afford the product (0.59 g, 78%) as snow-white needles. $^1$H NMR: δ 4.68 (s, 2H), 7.48 (d, J=8.5), 2H), 7.87 (d, J=8.5, 2H). $^{13}$C NMR: 846.09, 129.67, 130.37, 132.86, 140.98, 190.44.

EXAMPLE 4

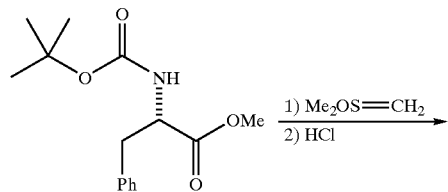

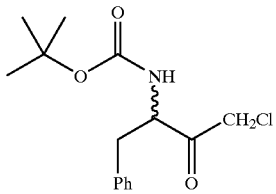

Dimethylsulfoxonium 2-oxo-3-(tert-butoxycarbonylamino)-4-phenylbutylide

A one liter flask equipped with a large stir bar, a reflux condenser and an argon inlet was wrapped with aluminum foil to exclude light. The flask was charged with trimethylsulfoxonium iodide (35.3 g, 160 mmol) and tetrahydrofuran (200 mL). To this suspension was added with stirring a 25 wt % solution of potassium t-amylate in THF (88 mL, 176 mmol) and the mixture was stirred 2 h at 70° C. The reaction mixture was cooled to 1° C. and a solution of N-(tert-butoxycarbonyl)-L-phenylalanine methyl ester (14.47 g, 51.8 mmol) in THF (80 mL) was added via cannula over 15 min so that the internal temperature remained between 1° and 5° C. After an additional 5 min at this temperature, the mixture was allowed to warm to room temperature over 30 min. After an additional 30 min, HPLC analysis of an aliquot diluted with 1 mL of acetonitrile and 5 drops of water showed complete consumption of the starting ester. The reaction was quenched with water (100 mL) and was stirred for 15 min after which the organic solvents were removed under vacuum. The concentrated mixture was further diluted with water (550 mL) and the product was extracted into dichloromethane (200 mL then 2×100 mL). The combined extracts were washed with water (2×200 mL), dried over magnesium sulfate, and concentrated under vacuum. Removal of residual solvents at high vacuum afforded the β-keto sulfur ylide (10.2 g, 59%) as a pale yellow solid. $^1$H NMR: δ 1.41 (s, 9H), 2.98 (m, 2H), 3.25 (s, 3H), 3.35 (s, 3H), 4.28 (s+m, 2H total), 5.22 (d, 1 H), 7.15–7.31 (m, 5H). A broad resonance at δ 1.90 indicated the presence of water even after drying for 1 h at 0.5 torr. $^{13}$C NMR: δ 28.05, 39.48, 41.46, 41.76, 57.56, 69.39, 79.01, 126.15, 127.86, 129.23, 137.36, 154.90, 186.39.

1-Chloro-3-(tert-butoxycarbonylamino)-4-phenyl-2-butanone

A one liter flask equipped with a large stir bar, a reflux condenser, and an argon inlet was charged with crude dimethylsulfoxonium 2-oxo-3-(tert-butoxycarbonylamino)-4-phenylbutylide (17.0 g, 50.0 mmol) and THF (250 mL). The mixture was cooled to 1° C. and lithium chloride was added in a single portion. Methanesulfonic acid (3.6 mL, 60 mmol) was added over 5 min so that the temperature remained between 1° and 3° C. after which the mixture was stirred at 65° C. for 4 h. (The reaction mixture was a thick slurry during the first 30 min.) The reaction was allowed to cool and was concentrated under vacuum to a solid/oil mixture. The mixture was taken up in ethyl acetate (170 mL) and was washed with half-saturated ammonium chloride (80 mL) and saturated sodium chloride (80 mL). The solution was dried with magnesium sulfate and the solvent was removed at reduced pressure to afford the crude chloroketone (14.5 g, 97%). The enantiomeric excess was determined to be <2% by supercritical fluid chromatography (Chiralcel OD-H, 250×4.6 mm, 5μ particle size, 3% methanol in CO$_2$ mobile phase, 40° C., 2 mL/min, 150 bar). Retention times for the enantiomers were assigned using an authentic racemate as 6.16 and 6.74 min. A portion (14.25 g) of the product was crystallized from hot 95:5 hexane/MTBE to afford pure product (11.9 g, 81%) as an off-white solid. $^1$H NMR: δ 1.40 (s, 9H), 2.94–3.12 (m, 2H), 4.00 (d, J=16.2, 1H), 4.18 (d, J=16.2, 1H), 4.68 (m, 1H), 5.10 (b, 1H), 7.14–7.47 (m, 5H). $^3$C NMR: δ 28.44, 37.78, 47.80, 58.68, 80.67, 127.51 129.10, 129.35, 135.88, 155.46, 201.65.

EXAMPLE 5

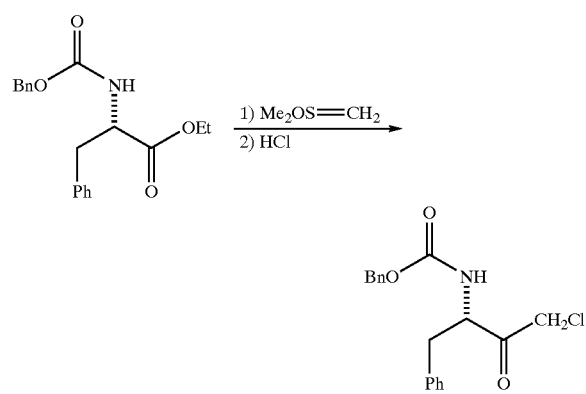

Dimethylsulfoxonium 2-oxo-3-(benzyloxycarbonylamino)-4-phenylbutylide

A flask was charged with trimethylsulfoxonium chloride (7.72 g, 60 mmol) and a 1.0 M solution of potassium tert-butoxide in tetrahydrofuran (63 mL, 63 mmol). Additional tetrahydrofuran (50 mL) was added and the mixture was heated to reflux for 2 h. The mixture was cooled to 0° C. and N-(benzyloxycarbonyl)-phenylalanine ethyl ester (6.54 g, 20 mmol) was added. After an additional 4 h at 0° C., the reaction was quenched by addition of water (20 mL). The organic layer was separated and washed with brine (2×10 mL). Distillation of the solvent afforded the product (4.40 g, 59%) as a white solid. $^1$H NMR: δ 3.03 (d, J=6.0, 2H), 3.23 (s, 3H), 3.32 (s, 3H), 0.30 (s, 1H), 4.40 (m, 1H), 5.09 (s, 2H), 5.72 (d, J=8.7, 1H), 7.30 (m, 10H). $^{13}$C NMR: δ 39.90, 41.88, 42.21, 58.51, 66.77, 69.97, 126.78, 128.23, 128.44, 128.69, 129.74, 136.83, 137.65, 155.92, 186.32.

1-Chloro-3-(benzyloxycarbonylamino)-4-phenyl-2-butanone

A solution of dimethylsulfoxonium 2-oxo-3-(benzyloxycarbonylamino)-4-phenylbutylide (2.40 g, 6.43 mmol) and lithium chloride (0.35 g, 8.0 mmol) in tetrahydrofuran (25 mL) was cooled to 0° C. and methanesulfonic acid (0.5 mL, 7.7 mmol) was added. The temperature was gradually raised to 70° C. over the course of 2 h. After cooling, the reaction was quenched with water (10 mL) and saturated sodium bicarbonate (10 mL) and extracted into ethyl acetate (30 mL). The organic phase was diluted with heptane (75 mL) and further washed with water (3×20 mL) and brine (20 mL) and was dried over sodium sulfate. Removal of the solvent afforded the crude product (2.33 g) as a white solid which was then crystallized from 4:1 hexane/ethyl acetate to give the pure chloroketone (1.88 g, 88%). The enantiomeric excess was determined to be <2% by supercritical fluid chromatography (Chiralcel OD-H, 250×4.6 mm, 5μ particle size, 3% methanol in CO$_2$ mobile phase, 40° C., 2 mL/min, 150 bar). $^1$H NMR: δ 3.10 (dd, J=16.6, 7.1, 2H), 4.02 (d, J=16, 1H), 4.08 (d, J=16.2, 1H), 4.78 (m, 1H), 5.10 (s, 2H), 5.43 (m, 1H), 7.32 (m, 10H). $^{13}$C NMR: δ 37.85, 47.69, 58.96, 67.48, 127.67, 128.34, 128.56, 128.81, 129.20, 129.34, 129.61, 135.50, 136.14, 156.01, 201.27.

EXAMPLE 6

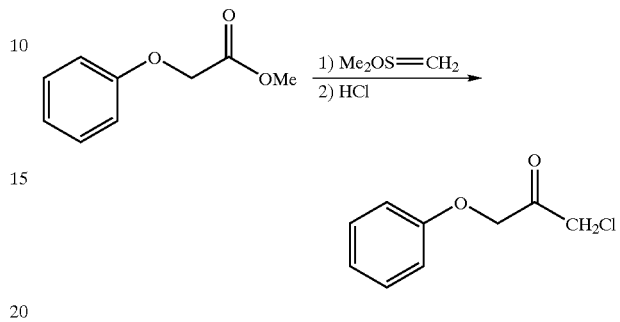

Dimethylsulfoxonium 2-oxo-3-(phenoxy)propylide

A 100 mL flask was charged with trimethylsulfoxonium chloride (3.90 g, 30 mmol), tetrahydrofuran (30 mL), and 1.0 M potassium tert-butoxide in THF solution (31.5 mL, 31.5 mmol). The suspension was heated at reflux for 2 h then cooled to room temperature. Methyl phenoxyacetate (1.66 g, 10 mmol) was added dropwise over 10 min whereupon the mixture was stirred overnight at room temperature. After distillation of the solvent, water (10 mL) was added and the product was extracted into ethyl acetate (2×50 mL). The organic phase was washed with brine (2×10 mL), dried over sodium sulfate, and concentrated in vacuum to afford the crude product (2.1 g). Recrystallization from ethyl acetate (10 mL) afforded the sulfur ylide (1.47 g, 65%) as a white crystalline solid. $^1$H NMR δ 3.40 (s, 6H), 4.38 (s, 2H), 4.90 (s, 1H), 6.83–6.96 (m, 3H), 7.24 (m, 2H). $^{13}$C NMR δ 41.8, 69.3, 70.3, 114.5, 121.0, 129.4, 158.0, 185.5.

1-Chloro-3-phenoxy-2-propanone

A glass tube was charged with crude dimethylsulfoxonium 2-oxo-3-(phenoxy)propylide (0.91 g, 4.0 mmol), THF (15 mL), and 4 M HCl in dioxane solution (1.15 mL, 4.6 mmol). The tube was sealed with a Teflon stopper and stirred at room temperature for 10 minutes then for 2 h in a 70° C. heated block at which time the mixture was homogeneous. After cooling, the solvent was removed at reduced pressure. The residue was added to water (15 mL) and extracted into methyl t-butyl ether (2×10 mL). Removal of the solvent afforded the product as a colorless oil (0.72 g, 97%) which crystallized upon standing to a low melting solid. $^1$H NMR: δ 4.27 (s, 2H), 4.60 (s, 2H), 6.77 (d, 2H), 6.90 (t, 1H), 7.19 (m, 2H). $^{13}$C NMR: δ 46.7, 71.3, 114.6, 121.6, 129.6, 157.1, 198.8.

It is to be understood that the foregoing description and examples are merely illustrative of the principles of the invention and that numerous other embodiments in accordance with this invention may be devised by one skilled in the art without departing from the spirit and scope thereof.

We claim:

1. A process for the preparation of α-chloroketones represented by the formula (I),

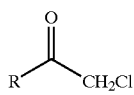

(I)

wherein R is alkyl or substituted alkyl, cycloalkyl or substituted cycloalkyl, aryl or substituted aryl, heterocycle or substituted heterocycle, provided that said heterocycle is attached to —(C=O)CH$_2$Cl in formula (I) at any available ring carbon atom, comprising
a) reacting an alkyl ester represented by the formula (II),

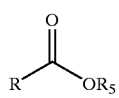

(II)

wherein R is as defined above, R$_5$ is alkyl or substituted alkyl, with a sulfoxonium ylide represented by the formula (III),

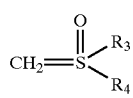

(III)

wherein R$_3$ and R$_4$ are selected from the group consisting of alkyl, substituted alkyl, aryl and substituted aryl,
to produce a keto sulfoxonium ylide represented by the formula (IV),

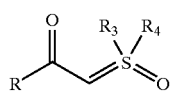

(IV)

wherein R, R$_3$ and R$_4$ are as defined as above; and
b) treating said keto sulfoxonium ylide with anhydrous HCl.

2. The process of claim 1, wherein R is alkyl or substituted alkyl, cycloalkyl or substituted cycloalkyl, aryl or substituted aryl, and R$_5$ is C$_1$–C$_4$ alkyl.

3. The process of claim 1, wherein R is alkyl or substituted alkyl, and R$_5$ is C$_1$–C$_4$ alkyl.

4. The process of claim 1, wherein R is aryl or substituted aryl, and R$_5$ is C$_1$–C$_4$ alkyl.

5. The process of claim 1, wherein R is phenyl or substituted phenyl, and R$_5$ is C$_1$–C$_4$ alkyl.

6. The process of claim 1, wherein R$_3$ and R$_4$ are each methyl, and R$_5$ is methyl or ethyl.

7. The process of claim 6, wherein R is alkyl or substituted alkyl.

8. The process of claim 6, wherein R is aryl or substituted aryl.

9. The process of claim 6, wherein R is phenyl or substituted phenyl.

10. The process of claim 6, wherein R is phenyl.

11. The process of claim 1, additionally including the step of forming said sulfoxonium ylide represented by the formula (III) by the reaction of a sulfoxonium salt with a base in an organic solvent.

12. The process of claim 1, wherein said sulfoxonium salt is a trialkyl sulfoxonium halide and said base is potassium tert-butoxide or potassium tert-amylate.

13. The process of claim 1, wherein the reaction of said keto sulfoxonium: ylide represented by formula (IV) with said anhydrous HCl is carried out in an organic solvent at a temperature of from about 60° C. to about 80° C.

14. A process in accordance with claim 13, where said solvent is at least one member selected from the group consisting of dimethylformamide, tetrahydrofuran, acetonitrile and toluene.

15. The process of claim 1, wherein said HCl is generated in situ by reacting a source of chloride and an organic acid.

16. The process of claim 15, wherein said source of chloride is lithium chloride.

17. The process of claim 16, wherein said organic acid is methanesulfonic acid.

18. The process of claim 1, wherein the reaction of said alkyl ester represented by formula (II) with said sulfoxonium ylide represented by formula (III) is carried out at a temperature of from about 0° C. to about 5° C. in an organic solvent.

19. The process of claim 18, wherein said solvent is tetrahydrofuran.

20. A process for the preparation of α-chloroketones represented by the formula (Ia),

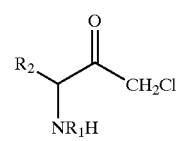

(Ia)

wherein R$_1$ is a protecting group for the amino function; R$_2$ is hydrogen, alkyl or substituted alkyl, cycloalkyl or substituted cycloalkyl, aryl or substituted aryl, heterocycle or substituted heterocycle, comprising reacting a methyl ester represented by the formula (IIa),

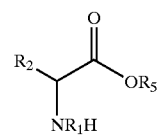

(IIa)

wherein R$_1$ and R$_2$ are as defined above, R$_5$ is alkyl or substituted alkyl, with a sulfoxonium ylide represented by the formula (III),

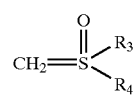

(III)

wherein R$_3$ and R$_4$ are selected from the group consisting of alkyl, substituted alkyl, aryl and substituted aryl, to produce a keto sulfoxonium ylide represented by the formula (IVa),

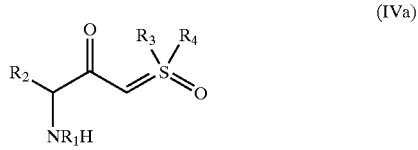

(IVa)

wherein $R_1$, $R_2$, $R_3$ and $R_4$ are defined as above, and treating said keto sulfoxonium ylide with anhydrous HCl.

21. A process of claim 20, wherein $R_2$ is hydrogen, alkyl or substituted alkyl, aryl or substituted aryl, and $R_5$ is $C_1$–$C_4$ alkyl.

22. A process of claim 20, wherein $R_1$ is tert-butoxycarbonyl (BOC) or benzyloxycarbonyl (CBZ), and $R_5$ is $C_1$–$C_4$ alkyl.

23. A process of claim 20, wherein $R_3$ and $R_4$ are each methyl, and $R_5$ is methyl or ethyl.

24. A process of claim 20, wherein $R_1$ is tert-butoxycarbonyl (BOC) or benzyloxycarbonyl (CBZ), and $R_2$ is hydrogen, alkyl or substituted alkyl, phenyl or substituted phenyl, and $R_5$ is $C_1$–$C_4$ alkyl.

25. A process of claim 24, wherein $R_3$ and $R_4$ are each methyl, and $R_5$ is methyl or ethyl.

26. A process of claim 25, wherein $R_2$ is methyl, isopropyl, or benzyl.

27. The process of claim 20, additionally including the step of forming said sulfoxonium ylide represented by the formula (III) by the reaction of a sulfoxonium salt with a base in an organic solvent.

28. The process of claim 27, wherein said sulfoxonium salt is a trialkyl sulfoxonium halide and said base is potassium tert-butoxide or potassium tert-amylate.

29. The process of claim 20, wherein the reaction of said keto sulfoxonium ylide represented by formula (IV) with said anhydrous HCl is carried out in an organic solvent at a temperature of from about 60° C. to about 80° C.

30. A process in accordance with claim 29, where said solvent is at least one member selected from the group consisting of dimethylformamide, tetrahydrofuran, acetonitrile and toluene.

31. The process of claim 20, wherein said HCl is generated in situ by reacting a source of chloride and an organic acid.

32. The process of claim 31, wherein said source of chloride is lithium chloride.

33. The process of claim 32, wherein said organic acid is methanesulfonic acid.

34. The process of claim 20, wherein the reaction of said alkyl ester represented by formula (II) with said sulfoxonium ylide represented by formula (III) is carried out at a temperature of from about 0° C. to about 5° C. in an organic solvent.

35. The process of claim 34, wherein said solvent is tetrahydrofuran.

36. A process for the preparation of a keto sulfoxonium ylide represented by the formula (IV),

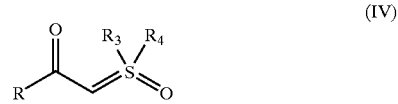

(IV)

wherein R is alkyl or substituted alkyl, cycloalkyl or substituted cycloalkyl, aryl or substituted aryl, heterocycle or substituted heterocycle, provided that said heterocycle is attached to —(C=O) group in formula (IV) at any available ring carbon atom; $R_3$ and $R_4$ are selected from the group consisting of alkyl, substituted alkyl, aryl and substituted aryl;

comprising reacting an alkyl ester represented by the formula (II),

(II)

wherein R is as defined above, $R_5$ is alkyl or substituted alkyl, with a sulfoxonium ylide represented by the formula (III),

(III)

wherein $R_3$ and $R_4$ are as defined above.

37. The process of claim 36, wherein R is alkyl or substituted alkyl, cycloalkyl or substituted cycloalkyl, aryl or substituted aryl, and $R_5$ is $C_1$–$C_4$ alkyl.

38. The process of claim 36, wherein R is alkyl or substituted alkyl, and $R_5$ is $C_1$–$C_4$ alkyl.

39. The process of claim 36, wherein R is aryl or substituted aryl, and $R_5$ is $C_1$–$C_4$ alkyl.

40. The process of claim 36, wherein R is phenyl or substituted phenyl, and $R_5$ is $C_1$–$C_4$ alkyl.

41. The process of claim 36, wherein $R_3$ and $R_4$ are each methyl, and $R_5$ is methyl or ethyl.

42. The process of claim 41, wherein R is alkyl or substituted alkyl.

43. The process of claim 41, wherein R is aryl or substituted aryl.

44. The process of claim 41, wherein R is phenyl or substituted phenyl.

45. The process of claim 44, wherein R is phenyl.

46. The process of claim 36, additionally including the step of forming said sulfoxonium ylide represented by the formula (III) by the reaction of a sulfoxonium salt with a base in an organic solvent.

47. Thr process of claim 46, wherein said sulfoxonium salt is a trialkyl sulfoxonium halide and said base is potassium tert-butoxide or potassium tert-amylate.

* * * * *